United States Patent [19]

Hoke

[11] Patent Number: 5,045,442

[45] Date of Patent: Sep. 3, 1991

[54] PHOTOGRAPHIC MATERIALS WITH NOVEL CYAN DYE FORMING COUPLERS

[75] Inventor: David Hoke, Rochester, N.Y.

[73] Assignee: Eastman Kodak Company, Rochester, N.Y.

[21] Appl. No.: 589,158

[22] Filed: Sep. 27, 1990

[51] Int. Cl.$^5$ .................................. G03C 7/34
[52] U.S. Cl. ...................... 430/553; 430/385
[58] Field of Search ..................... 430/553, 385

[56] References Cited

U.S. PATENT DOCUMENTS

| | | | |
|---|---|---|---|
| 2,949,360 | 8/1960 | Julian | 430/546 |
| 4,205,990 | 6/1980 | Deguchi et al. | 430/553 |
| 4,333,999 | 6/1982 | Lou | 430/552 |
| 4,489,155 | 12/1984 | Sakanoue et al. | 430/553 |
| 4,729,944 | 3/1988 | Mihayashi et al. | 430/553 |
| 4,775,616 | 10/1988 | Kilminster et al. | 430/553 |
| 4,849,328 | 7/1989 | Hoke et al. | 430/553 |
| 4,865,961 | 9/1989 | Miura et al. | 430/553 |
| 4,910,128 | 3/1990 | Kamio et al. | 430/553 |
| 4,923,791 | 5/1990 | Merkel et al. | 430/553 |
| 4,957,853 | 9/1940 | Kobayashi et al. | 430/553 |

OTHER PUBLICATIONS

Mees and James, The Theory of the Photographic Process, 3rd edition, 1966, p. 393.

*Primary Examiner*—Richard L. Schilling
*Attorney, Agent, or Firm*—Joshua G. Levitt

[57] ABSTRACT

Photographic materials contain cyan dye forming couplers having good ethyl acetate solubility. The coupler contains a coupling off group with an asymmetric carbon atom. Manufacture of the material is simplified and in some instances the activity of the coupler is increased.

5 Claims, No Drawings

PHOTOGRAPHIC MATERIALS WITH NOVEL CYAN DYE FORMING COUPLERS

This invention relates to photographic materials containing a cyan dye forming coupler. In a particular aspect it relates to such materials, and methods of preparing them, in which cyan dye forming couplers are employed that have good solubility characteristics in ethyl acetate.

Most modern color photographic materials contain silver halide and a dye forming compound commonly called a coupler. An image is formed by reaction between oxidized silver halide developing agent and the coupler compound to form a dye. In most materials, the coupler compound is incorporated in a layer of the photographic material during manufacture and is rendered immobile in the layer as a result of the bulk provided by a ballast group on the coupler compound. Incorporation of the coupler is accomplished by dispersing it in a high-boiling organic solvent. Use of low-boiling auxiliary solvents, such as ethyl acetate, has become common practice. Reference is made to Mees and James, *The Theory of the Photographic Process*, 3rd edition, The McMillan Company, New York 1966, page 393, and Julian U.S. Pat. No. 2,949,360 for further details regarding incorporation of couplers.

The use of ethyl acetate as an auxiliary solvent is desirable because its low-boiling point readily permits removable by evaporation. This facilitates the manufacturing process by eliminating a washing step, which is required to remove higher boiling auxiliary solvents.

Recently, there have been discovered cyan dye forming couplers which have good dye characteristics. These are described in Lau U.S. Pat. No. 4,333,999 issued June 8, 1982, Kilminster et al. U.S. Pat. No. 4,775,616, Hoke et al. U.S. Pat. No. 4,849,328, and Merkel et al. U.S. Pat. No. 4,923,791.

While these couplers are advantageous for a number of reasons, including their spectral absorption characteristics, they are not as soluble in ethyl acetate as would be desired. This complicates the manufacture of photographic elements containing such couplers. Accordingly, it would be desirable to provide cyan couplers having improved ethyl acetate solubility.

I have found that this can be accomplished by employing as the coupling off group in a cyan dye forming coupler a group which contains an asymmetric carbon atom. Couplers of my invention not only have good ethyl acetate solubility, but in many instances have enhanced activity compared with couplers containing a coupling-off group that does not have an asymmetric carbon atom.

Thus, in accordance with the present invention there is provided a photographic element comprising a support bearing a silver halide emulsion layer having associated therewith a cyan dye forming coupler having in the coupling position a group containing an asymmetric carbon atom.

In accordance with another embodiment of this invention, there is provided a method for preparing a photographic element which comprises the steps of (a) dispersing, in an ethyl acetate auxiliary coupler solvent a cyan dye forming coupler having in the coupling position a group containing asymmetric carbon atom, (b) combining the dispersion formed in step (a) with a silver halide emulsion, (c) evaporating from the product of step (b) the ethyl acetate, and (d) coating the combined emulsion dispersion on a photographic support material.

Preferred couplers useful in this invention can be represented by the structural formula:

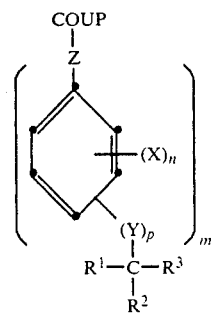

wherein
m is 0 or 1;
n is an integer of 0 through 4;
p is 0 or 1;
COUP is a cyan dye forming coupler moiety;
Z is oxygen or sulphur;
X is selected from the halogen (such as chloro, bromo and fluoro) nitro, cyano, alkyl of 1-12 carbon atoms, alkoxy of 1-12 carbon atoms, $COR$, $SO_2R$, $SO_2NR$, $NRSO_2$, $CONR$ and $NCOR$, wherein R is hydrogen, alkyl of 1-12 carbon atoms, alkoxy of 1-12 carbon atoms, aryl of 6-20 carbon atoms, or aryloxy of 6-20 carbon atoms, or two adjacent X groups complete a fused 5 to 7 membered carbocyclic or heterocyclic ring system comprised of carbon, nitrogen, oxygen and sulfur ring atoms;
Y, when m is 0, is

alkylene of 1-20 carbon atoms,

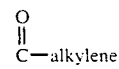

of 1-20 carbon atoms;

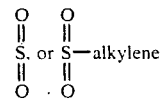

of 1 to 20 carbon atoms;

S arylene of 6-20 carbon atoms;
Y, when m is 1, is O, $SO_2$,

NR, SO₂NR, CONR, NRCO, NRSO₂, or alkylene of 1-20 carbon atoms where R is as defined above;

R¹, R², R³ are each different and are selected from hydrogen, alkyl of 1-20 carbon atoms, aryl of 6 to 20 carbon atoms, alkaryl or aralkyl of 7-20 carbon atoms,

SO₂R, SO₂NR, NRCO,

OCR, NRSO₂ where R is as defined above, or one of R¹, R² and R³ is a 5 to 7 membered heterocyclic ring system containing 1 to 3 rings each comprised of carbon, nitrogen, oxygen and sulfur ring atoms.

The coupling off groups of the present invention are advantageously employed with any cyan dye-forming coupler. Useful COUP groups include both naphtholic and phenolic cyan dye-forming couplers including those described in U.S. Pat. Nos. 2,772,162; 3,476,563; 4,526,864; 4,500,635; 4,254,212; 4,296,200; 4,457,559; 2,895,826; 3,002,836; 3,034,892; 2,474,293; 2,801,171; 2,423,730; 2,367,531; 3,041,236; 4,443,536; 4,333,999; 4,124,396; 4,775,616; 3,779,763; 3,772,002; 3,419,390; 4,690,889; 3,996,253; as well as those described in "Farbkuppler-eine Literaturübersicht," published in Agfa Mitteilungen, Band III, pp. 156-175 (1961).

The cyan dye-forming coupler is preferably a phenolic coupler moiety and most preferably is one which contains a ballast group in the five position and an amido or ureido group in the two position. Preferred such couplers are described in U.S. Pat. Nos. 4,333,999, 4,450,228, 4,617,255, 4,775,616, 4,849,328, 4,923,791 and 4,564,586; in European Published Patent Application No. 0 067 689, 0 073 145, 0 073 146, 0 148 536, 0 163,314, 0 164 030, and 0 175 573; and in German OLS 3,429,576.

Especially preferred couplers of this invention can be represented by the structure:

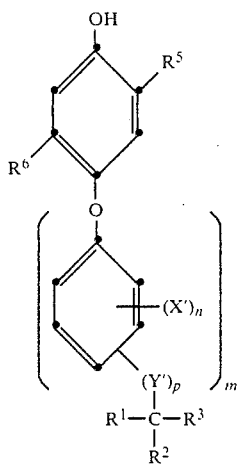

II.

wherein
m, n and p are each integers of 0 or 1;
R⁵ is an amido, or preferably, a ureido group,
R⁶ is a ballast group, preferably containing an asymmetric carbon atom, X' is halogen, nitro, alkyl of 1-4 carbon atoms, alkoxy of 1-4 carbon atoms or cyano;

Y' is alkylene of 1-20 carbons, -alkylene

of 1-20 carbon atoms or -alkylene SO₂- of 1-20 carbon atoms.

Most especially preferred cyan dye-forming couplers of this invention are represented by the structure:

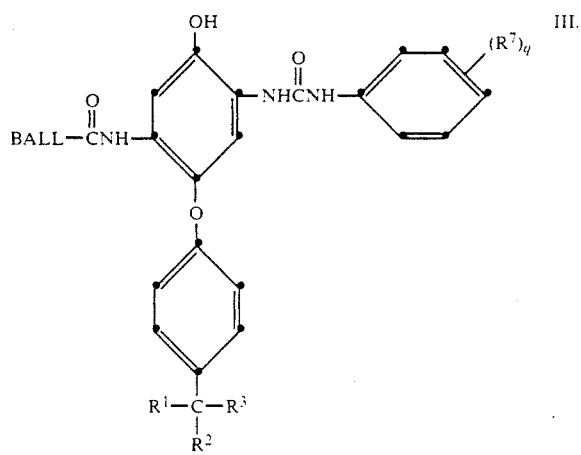

III.

wherein
R¹, R² and R³ are as defined above
q is an integer from 1-3
R⁷ is a cyano, halo, amidosulfonyl, sulfonamido, sulfoalkyl, sulfoaryl, fluorosulfonyl, alkyl, alkoxy, aryl or alkylthio; and
BALL is a ballast group containing an asymmetric carbon atom.

Representative couplers of this invention have the following structural formulae:

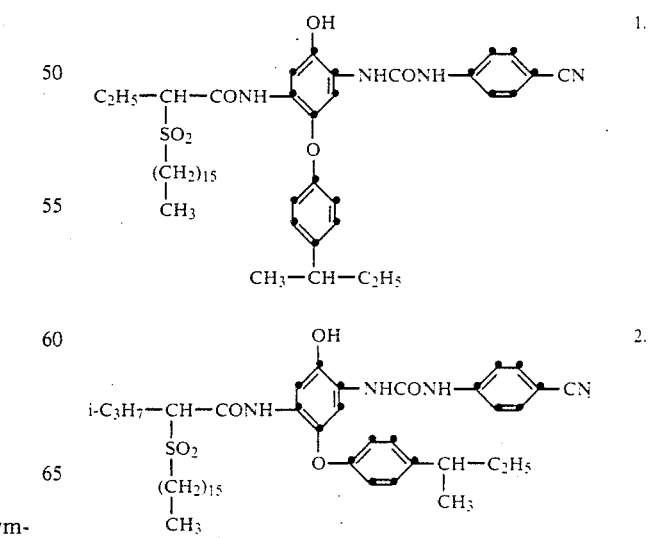

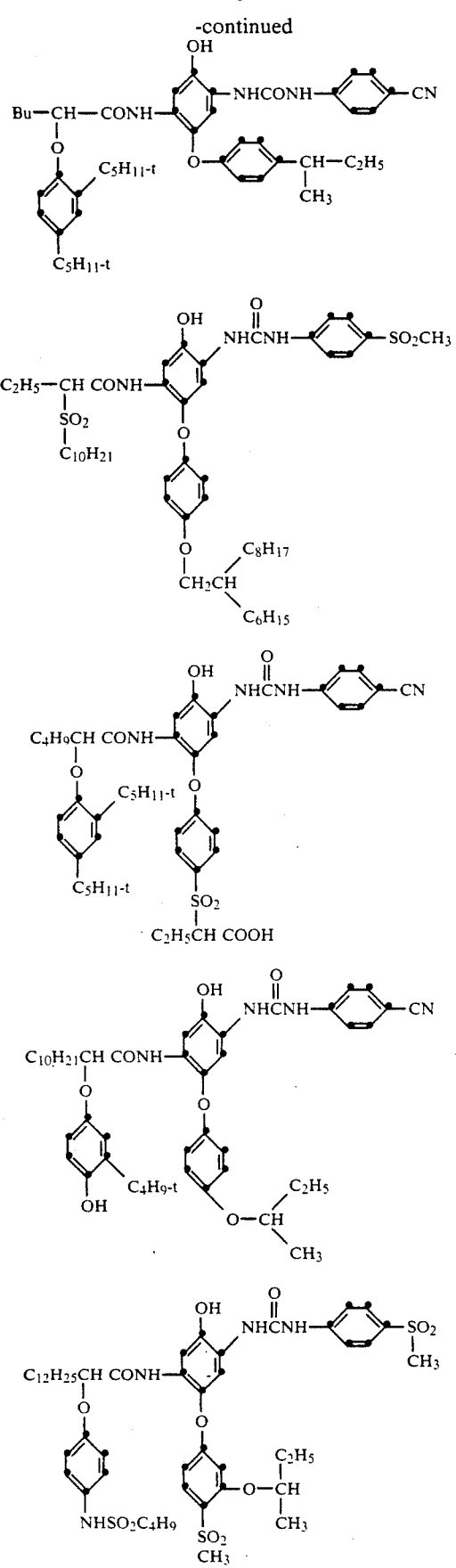

Couplers of this invention can be synthesized by techniques known in the art. Syntheses of the parent coupler are described in the patents cited above. Couplers of this invention can be prepared by a metathesis reaction between the chloro derivative of the parent coupler and the hydroxy or thiol derivative of the coupling off group. A representative synthesis is illustrated in Preparative Example 1, infra.

The couplers of this invention can be incorporated in silver halide emulsions and the emulsions can be coated on a support to form a photographic element. Details of techniques are well known in the art. Julian U.S. Pat. No. 2,949,360, referred to above, provides details regarding the use of ethyl acetate as an auxiliary solvent for dispersing the coupler. Alternatively, the coupler can be incorporated in photographic elements adjacent the silver halide emulsion where, during development, the coupler will be in reactive association with development products such as oxidized color developing agent. The coupler can be associated with an image modifying coupler, such as is described in Szajewski and Taber U.S. Ser. No. 534,829 filed June 7, 1990.

The photographic elements can be either single color or multicolor elements. In a multicolor element, the cyan dye-forming coupler is usually associated with a red-sensitive emulsion, although it could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler, a magenta image forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layer, interlayers, overcoat layers, subbing layers, and the like.

In the following discussion of suitable materials for use in the elements of this invention, reference will be made to *Research Disclosure*, December 1989, Item 308119, published by Kenneth Mason Publications, Ltd., The Old Harbourmaster's, 8 North Street, Emsworth, Hampshire P010 7DD, ENGLAND, the disclosures of which are incorporated herein by reference. This publication will be identified hereafter by the term "*Research Disclosure.*"

The silver halide emulsions employed in the elements of this invention can be comprised of silver bromide, silver chloride, silver iodide, silver chlorobromide, silver chloroidide, silver bromoiodide, silver chlorobromoiodide or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al U.S. Pat. No. 4,434,226, Daubendiek et al U.S. Pat. No. 4,414,310, Wey U.S. Pat. No. 4,399,215, Solberg et al U.S. Pat. No.

4,433,048, Mignot U.S. Pat. No. 4,386,156, Evans et al U.S. Pat. No. 4,504,570, Maskasky U.S. Pat. No. 4,400,463, Wey et al U.S. Pat. No. 4,414,306, Maskasky U.S. Pat. Nos. 4,435,501 and 4,643,966 and Daubendiek et al U.S. Pat. Nos. 4,672,027 and 4,693,964. Also specifically contemplated are those silver bromoiodide grains with a higher molar proportion of iodide in the core of the grain than in the periphery of the grain, such as those described in GB 1,027,146; JA 54/48,521; U.S. Pat. No. 4,379,837; U.S. Pat. No. 4,444,877; U.S. Pat. No. 4,665,012; U.S. Pat. No. 4,686,178; U.S. Pat. No. 4,565,778; U.S. Pat. No. 4,728,602; U.S. Pat. No. 4,668,614; U.S. Pat. No. 4,636,461; EP 264,954. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsions, i.e., emulsions that form latent images primarily on the surfaces of the silver halide grains, or internal latent image-forming emulsions, i.e., emulsions that form latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface sensitized. Noble metal (e.g., gold), middle chalcogen (e.g., sulfur, selenium, or tellurium), and reduction sensitizers, employed individually or in combination, are specifically contemplated. Typical chemical sensitizers are listed in *Research Disclosure*, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanines), oxonols, hemioxonols, styryls, merostyryls, and streptocyanines. Illustrative spectral sensitizing dyes are disclosed in *Research Disclosure*, cited above, Section IV.

Suitable vehicles for the emulsion layers and other layers of elements of this invention are described in Research Disclosure, Section IX and the publications cited therein.

In addition to the couplers described herein the elements of this invention can include additional couplers as described in Research Disclosure, Section VII, paragraphs D, E, F and G and the publications cited therein. These additional couplers can be incorporated as described in Research Disclosure Section VII, paragraph C and the publications cited therein.

The photographic elements of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section X), coating aids (Research Disclosure Section XI), plasticizers and lubricants (Research Disclosure Section XII), antistatic agents (Research Disclosure Section XIII), matting agents (Research Disclosure Section XVI) and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-$\beta$-(methanesulfonamido)ethylaniline sulfate hydrate, 4-amino-3-methyl-N-ethyl-N-$\beta$-hydroxyethylaniline sulfate, 4-amino-3-$\beta$-(methanesulfonamido)ethyl-N,N-diethylaniline hydrochloride and 4-amino-N-ethyl-N-(2-methoxyethyl)-m-toluidine di-p-toluene sulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples further illustrate this invention. In these examples, comparative couplers having the following structures were employed:

PREPARATIVE EXAMPLE 1

Preparation of Coupler 1

Synthesis 1

Coupler Compound No. 1 was pepared according to the following scheme:

A. Preparation of phenolic coupler moiety

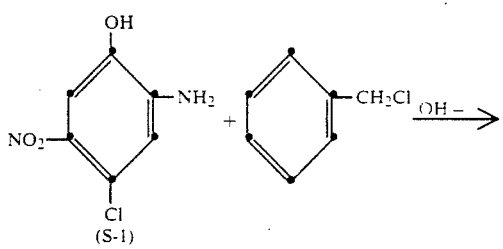

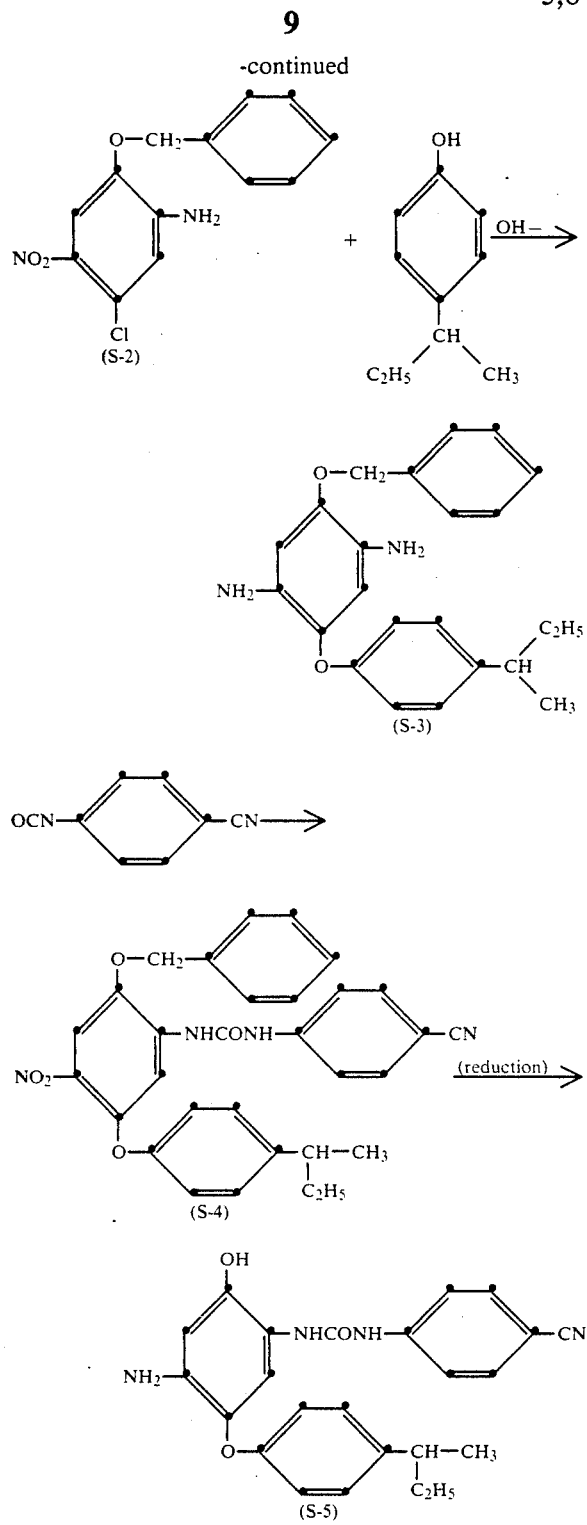

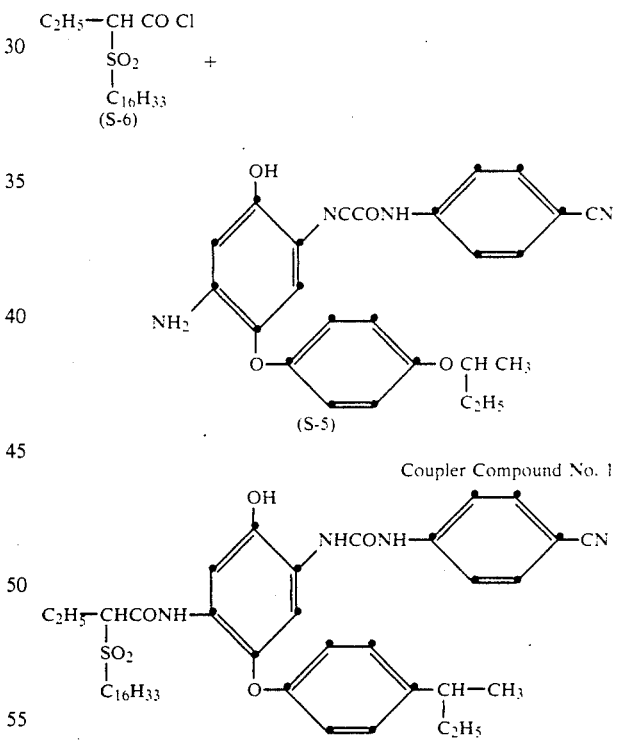

Preparation of 2-(p-cyanophenylureido)-4-p-sec-butyl-phenoxy-5-aminophenol (S-5)

To a refluxing solution of 33.7 g (0.2 mol) 2-amino-4-chloro-5-nitrophenol (S-1) and 12.8 g (0.2 mol) potassium hydroxide in 300 ml acetone was added over a 3 hour period 25.3 g (0.2 mol) α-chlorotoluene. After an additional 6 hour reflux, the mixture was concentrated and added to cold potassium carbonate solution. The resulting precipitate was washed, dried, and recrystallized from xylene to yield 44.8 g yellow-green solid S-2, m.p. 131°.

To a solution of 161 g (1.08 mol) p-sec-butylphenol dissolved in 500 ml pyridine is added a solution of 70 g (1.29 mol) sodium methoxide dissolved in 210 g methanol. The solvents were removed under vacuum to yield solid sodium salt of the phenol. The sodium salt was redissolved in 1000 ml dry pyridine. Added 330 g (1.18 mole) S-2 and refluxed for 16 hr. The pyridine was evaporated off and the residue was treated with 500 ml methanol. The solid product was filtered off, washed with 0° C. methanol and purified by column chromatography using silica gel as absorbent and dichloromethane as solvent to yield 205 g S-3 as a yellow solid.

This product was converted to S-4 by treatment with equimolar p-cyanophenylisocyanate according to a procedure analogous to that described in Example 1 of U.S. Pat. No. 4,333,999, the disclosure of which is incorporated herein by reference.

A suspension of 7.6 g (14.2 mmol) nitro compound S-4 in 150 ml ethylacetate was shaken overnight with 2 g 10% palladium on carbon catalyst and 1.0 ml acetic acid under 40 lb hydrogen pressure to provide the aminophenol S-5.

B. Coupler formation

Preparation of Coupler Compound No. 1

Under a nitrogen atmosphere 6.2 g (14.8 mmol) phenolic coupler moiety S-5, 5.4 g (44.4 mmol) dimethylaniline and 14.8 mmol S-6 acid chloride were mixed in 300 ml ethyl acetate and stirred for 30 min. Washing with dilute hydrochloric acid, purification through silica gel and crytallization from acetonitrile yielded 6.8 g Coupler Compound No. 1, m.p. 118°–120° C. Identity of the product was confirmed by elemental analysis, nmr and mass spectra.

The following examples illustrates ethyl acetate solubility of couplers of this invention compared with prior art couplers.

EXAMPLE 1

Ethyl Acetate Solubility

Couplers 1, 2, and 3, having the structures shown above, and analogous couplers C-1, C-2, and C-3, in which the substituent in the para position of the phenoxy coupling off group is a —$OCH_3$ group rather than a —$CH(CH_3)(C_2H_5)$ group, were tested for ethyl acetate solubility. 50 mg samples of each coupler is mixed with 25 mg of the coupler solvent di-n-butyl phthalate and 150 mg of the auxiliary coupler solvent ethyl acetate. The mixture is stirred for 5 minutes and heated to a temperature of up to 75° C., if necessary. If complete solution of the coupler is obtained, it is considered to be soluble in ethyl acetate. The couplers are shown in Table I and the results are shown in Table II.

TABLE II

| Coupler | Ethyl Acetate Solubility |
|---|---|
| 1 | Yes |
| 2 | Yes |
| 3 | Yes |
| C-1 | No |
| C-2 | No |
| C-3 | No |

EXAMPLE 2

Photographic Activity

Photographic elements were prepared by coating a cellulose acetate film support with a light-sensitive layer comprising a silver bromoiodide 96.5 mol % I emulsion at 0.91 g $Ag/m^2$; gelatin at 3.78 $g/m^2$ containing a cyan phenolic coupler identified in Table II.

Each coupler was dispersed with one half its weight of di-n-butyl phthalate coupler solvent and three times its weight of auxiliary coupler solvent. For couplers 1, 2 and 3 ethyl acetate is the auxiliary solvent, and the ethyl acetate evaporates from the coating as it passes

TABLE I

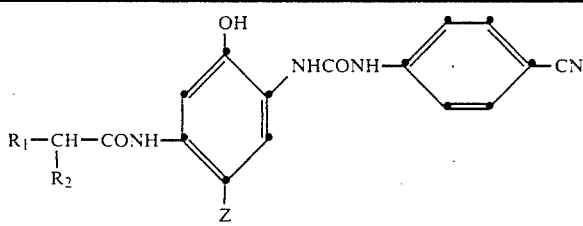

| Coupler Compound | $R_1$ | $R_2$ | Z |
|---|---|---|---|
| C-1 | —$C_2H_5$ | —$SO_2C_{16}H_{33}$ | —O—⟨phenyl⟩—$OCH_3$ |
| C-2 | —$C_3H_7$-i | —$SO_2C_{16}H_{33}$ | —O—⟨phenyl⟩—$OCH_3$ |
| C-3 | —$C_4H_9$ | —O—⟨phenyl with two $C_5H_{11}$-t⟩ | —O—⟨phenyl⟩—$OCH_3$ |
| 1 | —$C_2H_5$ | —$SO_2C_{16}H_{33}$ | —O—⟨phenyl⟩—$CH(C_2H_5)(CH_3)$ |
| 2 | —$C_3H_7$-i | —$SO_2C_{16}H_{33}$ | —O—⟨phenyl⟩—$CH(C_2H_5)(CH_3)$ |
| 3 | —$C_4H_9$ | —O—⟨phenyl with two $C_5H_{11}$-t⟩ | —O—⟨phenyl⟩—$CH(C_2H_5)(CH_3)$ | through the drying oven. For comparison couplers C-1, C-2 and C-3, which are not soluble in ethyl acetate, cyclohexanone was used as the auxiliary coupler solvent. Since it is not sufficiently voltaile to be removed during drying, it is removed by washing the chilled dispersion 4–6 hours with chilled (5°–6° C.) water. Each dispersion is coated at a rate which provides $1.62 \times 10^{-3}$ mol/m² of coupler. The photosensitive layer was overcoated with a layer containing gelatin at 1.08 g/m² and the hardener compound bis-(vinylsulfonylmethyl)ether at 1.75 weight percent on total gelatin.

Samples of each element were imagewise exposed through a graduated-density test object and processed at 40° C., employing the following color developing solution, with and without 7 g of citrazinic acid (CZA).

| Developer Solution | |
|---|---|
| K₂SO₃ | 2.0 g |
| K₂CO₃(anhydrous) | 30.0 g |
| KBr | 1.25 g |
| KI | 0.6 mg |
| 4-Amino-3-methyl-N-ethyl N-β-hydroxyethylaniline sulfate | 3.55 g |
| Water to 1.0 liter | ph 10.0 |

The elements were then stopped, bleached with a ferric EDTA 9 (ethylenediaminetetraacetic acid) solution, fixed, and washed to produce stepped cyan dye images.

From the steps cyan dye images are constructed curves of density vs. log exposure and from these curves are measured contrast at a density of 0.2 units above minimum density. The results are shown in Table III below.

TABLE III

| Coupler | Contrast(α) (without CZA competer) | Contrast(αCZA) with CZA competer) | αCZA/α |
|---|---|---|---|
| 1 | 1.27 | 0.87 | 0.685 |
| 2 | 1.07 | 0.60 | 0.561 |
| 3 | 0.97 | 0.60 | 0.619 |
| C-1 | 1.33 | 0.47 | 0.353 |
| C-2 | 1.03 | 0.67 | 0.650 |
| C-3 | 0.83 | 0.40 | 0.482 |

The enhanced activity of inventive couplers 1 and 3 compared with analogous comparison couplers C-1 and C-3 is illustrated by the lesser reduction in contrast in the presence of the CZA competing coupler.

The invention has been described in detail with particular reference to preferred embodiments thereof, but it will be understood that variations and modifications can be effected within the spirit and scope of the invention.

What is claimed is:

1. A photographic element comprising a support bearing a silver halide emulsion layer having associated therewith a cyan dye forming coupler having the structure

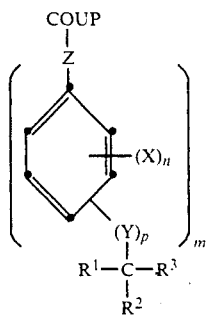

wherein m is 1;

n is an integer of 0 through 4;

p is 0 or 1;

COUP is a phenolic or naphtholic cyan dye forming coupler moiety;

Z is oxygen or sulphur;

X is selected from halogen, nitro, cyano, alkyl of 1–12 carbon atoms, alkoxy of 1–12 carbon atoms, COR, SO₂R, SO₂NR, NRSO₂ and CONR, NCOR wherein R is hydrogen, alkyl of 1–12 carbon atoms, alkoxy of 1–12 carbon atoms, aryl of 6–20 carbon atoms, or aryloxy of 6–20 carbon atoms, or two adjacent X groups complete a fused 5 to 7 membered carbocyclic or heterocyclic ring system comprised of carbon, nitrogen, oxygen and sulfur ring atoms;

Y is O, SO₂,

NR, SO₂NR, CONR, or alkylene of 1–20 carbon atoms where R is as defined above;

R¹, R², R³ are each different and are selected from hydrogen, alkyl of 1–20 carbon atoms, aryl of 6 to 20 carbon atoms, alkaryl or aralkyl of 7–20 carbon atoms,

SO₂R, SO₂NR, where R is as defined above or is a 5 to 7 membered heterocyclic ring system containing 1 to 3 rings each comprised of carbon, nitrogen, oxygen and sulfur ring atoms.

2. An element of claim 1, wherein COUP is a phenolic cyan dye forming coupler moiety.

3. An element of claim 1, wherein the cyan dye forming coupler has the structure

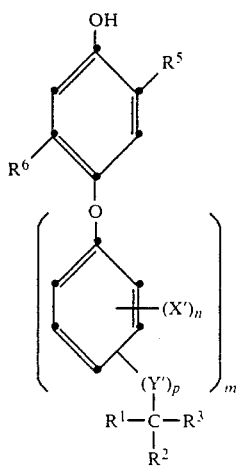

wherein m is 1, and n and p are each integers of 0 or 1;

$R^5$ is an amido, or a ureido group, $R^6$ is a ballast group,

X' is halogen, nitro, alkyl of 1-4 carbon atoms, alkoxy of 1-4 carbon atoms or cyano, and Y' is alkylene of 1 -20 carbons or

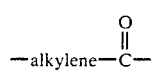

of 1 -20 carbon atoms.

4. An element of claim 1 wherein the cyan dye forming coupler has the structure

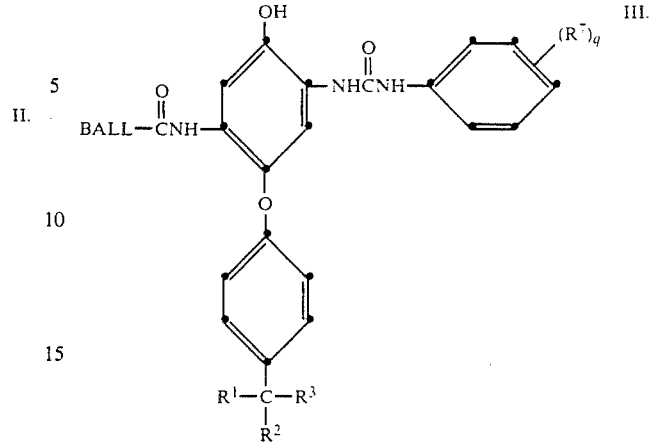

wherein
$R^1$, $R^2$ and $R^3$ are as defined above
q is an integer from 1–3
$R^7$ is cyano, halo, amidosulfonyl, sulfonamido, fluorosulfonyl, alkyl, alkoxy, aryl or alkylthio; and
BALL is a ballast group containing an asymmetric carbon atom.

5. An element of claim 4 wherein the cyan dye forming coupler is selected from the group consisting of:

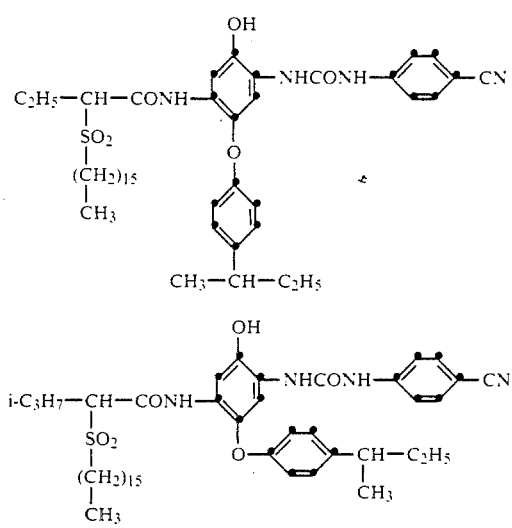

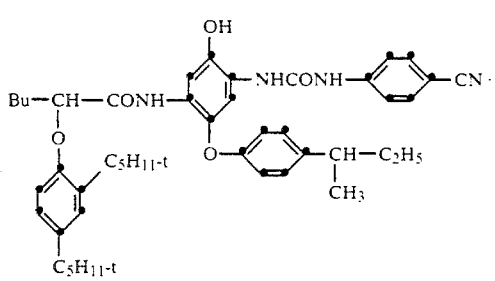

* * * * *